United States Patent [19]

Costantini et al.

[11] Patent Number: 5,414,153
[45] Date of Patent: May 9, 1995

[54] HYDROXYLATION OF PHENOLIC COMPOUNDS

[75] Inventors: Michel Costantini; Dominique Laucher, both of Lyons, France

[73] Assignee: Rhone-Poulenc Chimie, Courbevoie Cedex, France

[21] Appl. No.: 42,527

[22] Filed: Apr. 5, 1993

[30] Foreign Application Priority Data

Apr. 3, 1992 [FR] France ................. 92 04061

[51] Int. Cl.⁶ ............... C07C 37/60; C07C 39/08; C07C 39/16; C07C 39/27
[52] U.S. Cl. ................. 568/771; 558/271; 560/61; 564/179; 568/23; 568/629; 568/650; 568/723; 568/733; 568/737; 568/765; 568/766
[58] Field of Search ............ 568/771, 629, 650, 23, 568/723, 733, 737, 765, 766; 560/61; 558/271; 564/179

[56] References Cited

U.S. PATENT DOCUMENTS 4,078,006 3/1978 Umemura et al. ........... 568/766
4,174,460 11/1979 Seifert et al. ............... 568/771

FOREIGN PATENT DOCUMENTS 0132783 2/1985 European Pat. Off.
2266683 10/1975 France .

OTHER PUBLICATIONS

Chemical Abstracts, vol. 79, No. 5, Aug. 6, 1973, abstract No. 31665f, Inoue et al, "Oxidation of Phenol", p. 423, col. 2; & JP-A-73 036 130 (Toa Gosei Chemical Industry Co.) May 28, 1973.

*Primary Examiner*—Joseph E. Evans
*Attorney, Agent, or Firm*—Burns, Doane, Swecker & Mathis

[57] ABSTRACT

Phenolic compounds, e.g., the phenols and phenol ethers, are selectively hydroxylated whereby the amounts of the final product para isomer are enhanced, for example in favor of hydroquinone versus pyrocatechol in the event of the hydroxylation of phenol, by reacting such phenolic compounds with hydrogen peroxide, advantageously in a polar, aprotic, organic solvent reaction medium, in the presence of a catalytically effective amount of a sulfonated polymer and a cocatalytically effective amount of an aromatic ketone compound.

31 Claims, No Drawings

HYDROXYLATION OF PHENOLIC COMPOUNDS

BACKGROUND OF THE INVENTION

1. Field of the Invention

The present invention relates to the hydroxylation of phenolic compounds and, more especially, to the hydroxylation of phenols and phenol ethers by reacting same with hydrogen peroxide in the presence of a sulfonated polymer/ketone catalyst system.

2. Description of the Prior Art

Serious need exists in this art, for example for a selective process for the hydroxylation of phenol into hydroquinone and pyrocatechol that predominantly favors the production of hydroquinone.

The processes presently known to this art predominantly favor the production of pyrocatechol.

It is recognized that, in order to respond to the fluctuating requirements of the commercial market, an industrial process would be desirable that increased the production of hydroquinone relative to the amount of pyrocatechol.

Also, those processes currently in use entail conducting the hydroxylation via homogeneous catalysis.

For example, FR-A-2,071,464 describes a very important industrial process for the hydroxylation of phenols and phenol ethers.

Such process includes carrying out the hydroxylation, using hydrogen peroxide, in the presence of a strong acid. Among these strong acids, sulfuric acid, para-toluene sulfonic acid and perchloric acid are the most widely used.

The hydroxylation of phenol conducted under the operating conditions described produces a mixture of hydroquinone and pyrocatechol, with a predominance of the latter, since the hydroquinone/pyrocatechol ratio typically ranges from 0.3 to 0.7.

Pyrocatechol is thus produced in major amounts.

Although this process is very useful, it presents the disadvantage of being predicated upon homogeneous catalysis and concomitant problem of how to eliminate the acid catalyst at the end of the reaction. To eliminate the acid, it can be separated out [Ind. Eng. Chem. Prod. Res. Dev., 5, No. 3 (1976)] by aqueous washing and then the reaction medium can be treated with a mixture of water and isopropyl ether. The residual acid in the aqueous phase and the phenol and diphenols formed are extracted with isopropyl ether. It is then necessary to separate the isopropyl ether by distillation, followed by distillation of the phenol and diphenols.

FR-A-2,266,683 describes the hydroxylation of phenol in the presence of a ketone. Such process improves the yield of the reaction in respect of the hydroquinone and pyrocatechol. However, in all of the examples a larger amount of pyrocatechol is produced relative to that of hydroquinone.

And FR-A-2,667,598 describes a hydroxylation process wherein the amount of hydroquinone relative to the amount of pyrocatechol is increased and, in a preferred embodiment thereof, more hydroquinone than pyrocatechol is produced.

Said '598 process entails the hydroxylation of phenol in the presence of a catalytically effective amount of a strong acid, the reaction also being carried out in the presence of a ketone compound selected from among benzophenone and those benzophenones in which the hydrogen atoms of the aromatic nucleus are substituted by an electron-donor group.

In accordance with this process described in FR-A-2,667,598, the presence of the ketone compound during the hydroxylation of the phenol affects the selectivity of the reaction and hydroquinone/pyrocatechol ratios ranging from 1.0 to 1.13 are advantageously obtained.

However, such a process also presents the problem of eliminating the acid catalyst because it entails homogeneous catalysis employing a strong acid.

SUMMARY OF THE INVENTION

Accordingly, a major object of the present invention is the provision of an improved process for the hydroxylation of phenolic compounds, wherein, e.g., the amount of hydroquinone formed is significantly increased and the acid catalyst can easily be separated from the reaction medium upon completion of the reaction.

Another object of the present invention is the provision of an improved such hydroxylation process that comprises heterogeneous catalysis and which permits more hydroquinone than pyrocatechol to be produced.

Briefly, the present invention features a process for the hydroxylation of phenolic compounds having at least one hydrogen atom in the para- position of the hydroxyl group, comprising reacting such phenolic compound with hydrogen peroxide, in the presence of an acid catalyst, said acid catalyst comprising a catalytically effective amount of a polymer bearing sulfonic acid substituents and a ketone compound having the general formula (II):

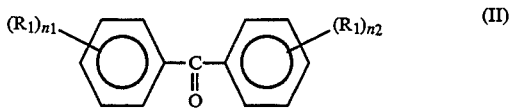

in which $R_1$ and $R_2$, which may be identical or different, are each a hydrogen atom or an electron-donor group; $n_1$, $n_2$, which may be identical or different, are each a number equal to 0, 1, 2 or 3; with the proviso that the two carbon atoms situated in the alpha position relative to the two carbon atoms bearing the —CO functional group can optionally be bonded together via a valence bond or by a —CH$_2$— bridge, thus forming a ketone ring member which can either be saturated or unsaturated.

DETAILED DESCRIPTION OF PREFERRED EMBODIMENTS OF THE INVENTION

More particularly according to the present invention, a heterogeneous catalytic system is required which comprises a polymer bearing sulfonic acid groups.

A wide variety of sulfonic acid polymers are commercially available and such resins are marketed under various trademarks. The following resins are exemplary thereof: TEMEX 50, AMBERLYST 15, AMBERLYST 35, AMBERLYST 36, DOWEX 50W.

The aforesaid resins which are well suited according to the present invention comprise a polystyrene skeleton or backbone substituted by sulfonic acid functional groups.

The polystyrene skeleton is obtained by polymerization of styrene and divinylbenzene, under the influence of an activation catalyst, typically an organic peroxide, to produce a crosslinked polystyrene. The polymerization is typically carried out in suspension and polymer beads or granules are obtained. These are treated with concentrated sulfuric or sulfochloric acid. A sulfonated styrene divinylbenzene copolymer is thus produced.

It is also possible to employ sulfonic resins which are phenol formaldehyde copolymers and which bear a methylene sulfonic acid substituent on the aromatic nucleus. Exemplary of such resins are those marketed under the trademark DUOLITE ARC 9359.

Other suitable resins are also available commercially, including the perfluorinated resins bearing sulfonic acid substituents and, more particularly, the resin NAFION which has the general structure given below:

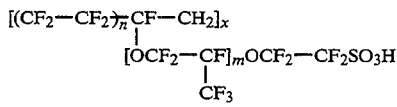

in which m is an integer equal to 1, 2, 3 and higher, n is a number ranging from 5 to 13.5 and x is equal to about 1,000. NAFION is prepared from a copolymer of tetrafluoroethylene and perfluoro[2-(fluorosulfonylethyoxy)-propyl]vinyl ether.

The subject resins can be of gel type or macrocrosslinked type. They are employed in the acid form.

Numerous resins are products which are available on the market in dry or wet form. Either of the forms can be used in the process of the invention.

They are typically in the form of approximately spherical particles having a diameter which ranges from 0.3 to 1.5 mm, preferably from 0.5 to 1.2 mm.

The resins indicated specifically above are preferably used in the process of the invention, and more preferably, those resins comprising a polystyrene skeleton. However, it is also within the scope of the invention to employ resins having a skeleton of another nature, provided it is substituted by the appropriate sulfonic groups.

The proportion of sulfonic functional groups relative to the polymer weight can vary and this is taken into consideration during the determination of the amount of polymer to be used.

The concentration of acid sites of the sulfonic polymer advantageously ranges from 1 to 10 milliequivalents of H+ ions per gram of dry polymer, and, preferably, from 2 to 7 milliequivalents of H+ ions per gram of dry polymer.

Another characteristic of the process of the invention is carrying out same in the presence of a ketone compound having the aforesaid formula (II), preferably benzophenone or a benzophenone substituted by an electron-donor substituent.

By "electron-donor group" or "substituent" is intended a group as defined by H. C. Brown in the text by Jerry March, *Advanced Organic Chemistry*, chapter 9, pages 243 and 244 (1985).

Consistent herewith, an electron-donor group is selected that does not react under the acid conditions of the invention.

Exemplary electron-donor groups which are suitable according to the present invention include:
  (i) linear or branched alkyl radicals having from 1 to 4 carbon atoms;
  (ii) the phenyl radical;
  (iii) $R_3$—O— alkoxyl radicals, in which $R_3$ is a linear or branched alkyl radical having from 1 to 4 carbon atoms or the phenyl radical;
  (iv) the hydroxyl group,
  (v) the fluorine atom.

Among the ketone compounds corresponding to general formula (II), preferred are those in which $R_1$ and $R_2$ are identical or different and each is a hydrogen atom or an electron-donor group, preferably in positions 4,4′, and $n_1$, $n_2$ are identical or different and are equal to 0 or 1.

The ketone compounds having formula (II) are more preferably those in which $R_1$ and $R_2$ are identical or different and each is a hydrogen atom, a methyl, ethyl, teritobutyl or phenyl radical, a methoxy or ethyoxy radical or a hydroxyl group, preferably in positions 3,3′ or 4,4′.

Particularly preferred ketones suitable for the process of the invention include:
  Benzophenone,
  2-Methyl benzophenone,
  2,4-Dimethyl benzophenone,
  4,4′-Dimethyl benzophenone,
  2,2′-Dimethyl benzophenone,
  4,4′-Dimethoxy benzophenone,
  Fluorenone,
  4-Hydroxybenzophenone,
  4,4′-Dihydroxylbenzophenone,
  4-benzoyl biphenyl.

In the process of the invention, the hydroxylation of a phenolic compound is carried out by reacting same with hydrogen peroxide.

By "phenolic compound" is intended an aromatic compound, of which one hydrogen atom directly bonded to the aromatic nucleus is replaced by a hydroxyl group and by "aromatic compound" is intended the standard definition of aromaticity as reported in the literature, in particular by Jerry March, *Advanced Organic Chemistry*, 3rd edition, pp. 37 et seq, John Wiley and Sons (1985).

The present invention is particularly applicable to the phenolic compounds having the general formula (I):

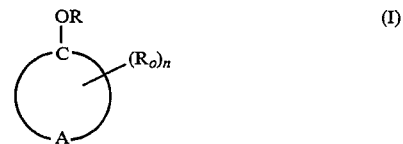

in which A is a residue of a monocyclic or polycyclic aromatic carbocyclic radical or a divalent radical comprising a chain of two or more monocyclic aromatic carbocyclic radicals; R is a hydrogen atom or a hydrocarbon radical having from 1 to 24 carbon atoms, for example, a linear or branched, saturated or unsaturated aliphatic radical or a saturated or unsaturated or aromatic, monocyclic or polycyclic cycloaliphatic radical; $R_O$ represents one or more identical or different substituents; and n is a number less than or equal to 4.

The process of the invention is applicable to any phenolic compound having the formula (I) and, more particularly, to the phenolic compounds of formula (I) in which R is a hydrogen atom, a linear or branched alkyl radical having from 1 to 6 carbon atoms, a cyclohexyl radical, a phenyl radical, a benzyl radical; the radical or radicals $R_O$ are each a hydrogen atom, a linear or branched alkyl radical having from 1 to 6 carbon atoms, a linear or branched alkenyl radical having from 2 to 6 carbon atoms, an alkoxy radical $R_4$—O, in which $R_4$ is a linear or branched alkyl radical having from 1 to 6 carbon atoms, an acyl radical having from 2 to 6 carbon atoms, a hydroxyl group, a —COOR$_5$ group, in which $R_5$ is a linear or branched alkyl radical having from 1 to 4 carbon atoms, a halogen atom, preferably fluorine, chlorine, as bromine, a —CF$_3$ group; and n is a number equal to 0, 1, 2 or 3.

The phenolic compound of formula (I) can bear one or more substituents. Exemplary substituents are indicated above but these are illustrative only. Any substituent may be present on the ring provided it does not interfere with production of the desired final product.

Exemplary compounds of formula (I) are those in which the residue (A) is:

(i) a monocyclic or polycyclic aromatic carbocyclic radical, the ring members of which can together form an orthocondensed system corresponding to formula (Ia):

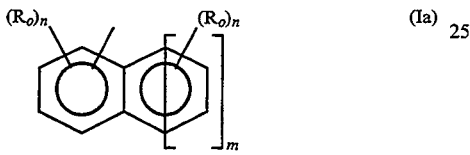

in which m is a number equal to 0, 1 or 2 and $R_O$ and n are as defined above;

(ii) a radical comprising a chain formation of two or more monocyclic aromatic carbocyclic radicals corresponding to the formula (Ib):

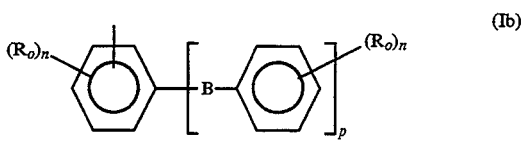

in which $R_O$ and n as defined above, p is a number equal to 0, 1, 2 or 3 and B is a valence bond, an alkylene or alkylidene radical having from 1 to 4 carbon atoms, preferably a methylene or isopropylidene radical, or one of the following groups:

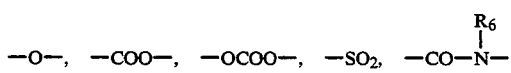

wherein $R_6$ is a hydrogen atom or an alkyl radical having from 1 to 4 carbon atoms, a cyclohexyl or phenyl radical.

The preferred compounds of formula (I) have the formulae (Ia) and (Ib), in which: $R_O$ is a hydrogen atom, a linear or branched alkyl or alkoxy radical having from 1 to 6 carbon atoms, preferably 1 to 4 carbon atoms, a cyclohexyl radical, a phenyl radical, or a hydroxyl group; B is a valence bond, an alkylene or alkylidene radical having from 1 to 4 carbon atoms or an oxygen atom; m is equal to 0 or 1; n is equal to 0, 1 or 2; and p is equal to 0 or 1.

More particularly preferred are the phenolic compounds of general formula (I'):

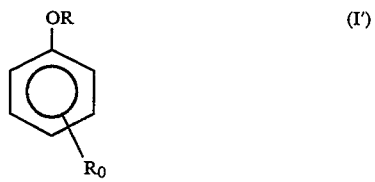

in which R and $R_O$, which may be identical or different, are each a hydrogen atom, an alkyl radical having from 1 to 4 carbon atoms, a cyclohexyl radical or a phenyl radical.

Even more preferred are the compounds of formula (I') in which R is a hydrogen atom and $R_O$ is a hydrogen atom, a methyl radical, or a methoxy radical.

Particularly representative phenolic compounds of formula (I) are:

(1) those in which the residue A corresponds to formula (Ia) wherein m and n are equal to 0, such as phenol or anisole;

(2) those in which the residue A corresponds to formula (Ia) wherein m is equal to 0 and n to 1, such as o-cresol, m-cresol, 2-methoxyphenol, 2-ethylphenol, 3-ethylphenol, 2-propylphenol, 2-sec-butylphenol, 2-tert-butylphenol, 3-tert-butylphenol, 2-methoxyphenol, 3-methoxyphenol, methyl salicylate, 2-chlorophenol, 3chlorophenol;

(3) those in which the residue A corresponds to formula (Ia) wherein m is equal to 0 and n is equal to 2, such as 2,3-dimethylphenol, 2,5-dimethylphenol, 2,6-dimethylphenol, 3,5-dimethylphenol, 2,6-di-tert-butylphenol, 3,5-di-tert-butylphenol, 2,3-dichlorophenol, 2,5-dichlorophenol, 2,6-dichlorophenol, 3,5-dichlorophenol;

(4) those in which the residue A corresponds to formula (Ia) wherein m is equal to 0 and n is equal to 3, such as 2,3,5-trimethylphenol, 2,3,6-trimethylphenol, 2,3,5-trichlorophenol, 2,3,6-trichlorophenol;

(5) those in which the residue A corresponds to formula (Ia) wherein m is equal to 1 and n is equal to 4, such as 1-hydroxynaphthalene;

(6) those in which the residue A corresponds to formula (Ib) wherein p is equal to 1, such as 2-phenoxyphenol, 3-phenoxyphenol.

The process of the present invention is particularly suitable for the preparation of hydroquinone and pyrocatechol from phenol.

In the process of the invention, the hydroxylation of the phenolic compound of formula (I) is carried out by means of hydrogen peroxide, in the presence of a catalytically effective amount of a sulfonic acid polymer and in the presence of a cocatalytically effective amount of a ketone compound of formula (II).

The amount of sulfonated polymer to be used is determined in such manner that the ratio of the number of proton equivalents to the number of moles of hydrogen peroxide ranges from about $1.10^{-4}$ to about 1.0.

In a preferred embodiment of the invention, an $H^+/H_2O$ ratio is selected ranging from $1.10^{-3}$ and 0.1.

As regards the ketone compound of formula (II), it is used in a catalytic amount. Generally, the amount of the ketone compound of formula (II), expressed in moles per mole of hydrogen peroxide, ranges from $1.10^{-3}$ mole to 10. The amount of ketone compound advantageously ranges from 0.05 to 5.0 moles, preferably from 0.05 to 1 mole, per mole of hydrogen peroxide.

The hydrogen peroxide employed in the process of the invention can be in the form of an aqueous solution, or an organic solution.

Aqueous solutions, which are the more readily available commercially, are preferably used.

The concentration of the aqueous solution of hydrogen peroxide, although not critical in and of itself, is selected such as to introduce as little water as possible into the reaction medium. An aqueous solution of hydrogen peroxide of at least 20% by weight of $H_2O_2$ is generally used and, preferably, of about 70%.

The amount of hydrogen peroxide can be up to 1 mole of $H_2O_2$ per 1 mole of phenolic compound of formula (I).

It is, however, preferable, in order to obtain an industrially acceptable yield, to employ a molar ratio of hydrogen peroxide/phenolic compound of formula (I) of 0.01 to 0.3 and, preferably, 0.05 to 0.10.

In order to achieve a sufficient reaction speed, the initial water content of the medium is limited to 20% by weight and, preferably, to 10% by weight.

The contents by weight indicated are expressed relative to the mixture of phenolic compound of formula (I)/hydrogen peroxide/water.

This initial water corresponds to the water introduced with the reagents and, in particular, with the hydrogen peroxide.

In a preferred embodiment of the invention a complexing agent for the metal ions present in the medium is added, because these are detrimental to the satisfactory progress of the process of the invention, in particular in the case of the phenols where the yields of hydroxylation products are low. Consequently, it is preferable to inhibit the action of the metal ions.

Metal ions which are detrimental to the progress of hydroxylation are transition metal ions and more particularly, iron, copper, chromium, cobalt, manganese and vanadium ions.

The metal ions emanate from the reagents and, in particular, the aromatic compounds and the apparatus utilized. In order to inhibit the action of these metal ions, it suffices to carry out the reaction in the presence of one or more complexing agents stable vis-à-vis hydrogen peroxide and producing complexes which cannot be decomposed by the strong acids present and in which the metal can no longer exercise any chemical activity.

Exemplary of these complexing agents are, in particular, the various phosphoric acids such as, for example, orthophosphoric acid, metaphosphoric acid, pyrophosphoric acid, polyphosphoric acids, phosphonic acids such as (1-hydroxyethylidene) diphosphonic acid, phosphonic acid, ethylphosphonic acid, phenylphosphonic acid.

The esters of the acids indicated above can also be used and exemplary thereof are, more particularly, mono- or dialkyl, mono- or dicycloalkyl, mono- or dialkylaryl orthophosphates, for example ethyl or diethyl phosphate, hexyl phosphate, cyclohexyl phosphate, benzyl phosphate.

The amount of complexing agent depends on the metal ion content of the reaction medium.

The amount of complexing agent, expressed in the number of moles of complexing agent per mole of hydrogen peroxide, advantageously ranges from 0.0001 to 0.01.

According to the present invention, the hydroxylation of the phenolic compound of formula (I) is carried out at a temperature advantageously ranging from 45° C. and 150° C.

In a preferred embodiment of the invention the process is carried out at a temperature ranging from 45° C. to 75° C.

The reaction is advantageously carried out under atmospheric pressure.

The hydroxylation is typically conducted without a solvent other than that which results from the reagents, such as the hydrogen peroxide solvent.

However, it has been determined that the addition of a certain amount of an aprotic, polar, organic solvent having certain characteristics of polarity and basicity, permits the para/ortho ratio to be increased and, more particularly, in the event of hydroxylation of phenol, permits the hydroquinone/pyrocatechol ratio to be increased in favor of the hydroquinone.

Two classes of organic solvents are suitable for carrying out the process of the invention.

Thus, in one embodiment of the process of the invention, the reaction is carried out in the presence of an aprotic, polar, organic solvent, having a polarity such that its dielectric constant is greater than or equal to 20 and a basicity such that it has a "donor number" of less than 25.

Several requirements affect the selection of the organic solvent.

A first characteristic of the organic solvent is that it is aprotic and stable in the reaction medium.

By "aprotic solvent" is intended a solvent which, according to Lewis's theory, has no protons to be released.

Solvents which are not stable in the reaction medium and which decompose either by oxidation or by hydrolysis are without the ambit of the present invention.

A second characteristic of the organic solvent is that it has a certain polarity. An organic solvent is selected which has a dielectric constant greater than or equal to 20. The upper limit is not critical. It is preferred to employ an organic solvent having a high dielectric constant, preferably ranging from 25 to 75.

In order to determine whether the organic solvent corresponds to the condition of the dielectric constant indicated above, *Techniques of Chemistry, II, Organic Solvents*, pp. 536 et seq, 3rd Edition (1970) sets forth tables suitable for such purpose.

A third characteristic of the organic solvent is that is has a basicity such that is has a "donor number" of less than 25, preferably less than or equal to 20. The lower limit is not critical. An organic solvent having a donor number ranging from 2 to 17 is preferably selected.

With respect to the requirements concerning the basicity of the organic solvent, it should be appreciated that the "donor number," abbreviated to DN, provides an indication of the extent of nucleophilicity of the solvent and reveals its ability to produce its doublet.

In the text by Christian Reinhardt, *Solvents and Solvent Effects in Organic Chemistry*, VCH p. 19 (1988), the definition of "donor number" is provided, which is defined as the negative ($-\Delta H$) of the enthalpy (Kcal/mol) of the interaction between the solvent and antimony pentachloride, in a dilute solution of dichloroethane.

Exemplary polar aprotic solvents having the characteristics indicated above, include, in particular:
(1) nitro compounds such as nitromethane, nitroethane, 1-nitropropane, 2-nitropropane or mixtures thereof, nitrobenzene;

(2) aliphatic or aromatic nitriles such as acetonitrile, propionitrile, butanenitrile, isobutanenitrile, benzonitrile, benzyl cyanide;

(3) tetramethylene sulfone (sulfolane);

(4) propylene carbonate.

A mixture of such solvents can also be used.

Among the solvents indicated above, acetonitrile is the preferred.

The amount of organic solvent to be used is determined in such manner that the molar ratio between the number of moles of organic solvent and the number of moles of phenolic compound of formula (I) ranges from 0.1 to 2.0, and preferably from 0.25 to 1.0.

Another embodiment of the process of the invention entails carrying out the reaction in the presence of a polar, aprotic, organic solvent having a polarity such that its dielectric constant is less than about 20 and a basicity such that it has a "donor number" greater than or equal to 15 and less than 25.

As indicated above, in the case of the other class of solvents previously described, the organic solvent must be aprotic and stable in the reaction medium.

Solvents which are not stable in the reaction medium and which decompose either by oxidation or by hydrolysis are also without the ambit of the present invention. Exemplary reaction solvents which are not suitable according to the invention includes solvents of the ester type derived from carboxylic acids such as, in particular, methyl or ethyl acetate, methyl or ethyl phthalate, methyl benzoate, and the like.

A second characteristic of the organic solvent is that it has a certain polarity. In accordance with the invention, an organic solvent is selected which has a dielectric constant of less than about 20. The lower limit is not critical. It is preferred to use an organic solvent having a low dielectric constant, preferably ranging from 2 to 15.

A third characteristic of the organic solvent is that is has a basicity such that it has a "donor number" greater than or equal to 15 and less than 25. An organic solvent having a donor number ranging from 15 to 25 is preferably selected.

Exemplary polar aprotic solvents having the characteristics indicated above include, in particular:

(1) aliphatic, cycoaliphatic or aromatic ether-oxides and, more particularly, diethyl oxide, dipropyl oxide, diisopropyl oxide, dibutyl oxide, methyltertiobutylether, dipentyl oxide, diisopentyl oxide, dimethylether of ethyleneglycol (or 1,2-dimethoxyethane), dimethylether of diethyleneglycol (or 1,5-dimethoxy-3-oxapentane), dioxane, tetrahydrofuran;

(2) neutral phosphoric esters such as, in particular, trimethyl phosphate, triethyl phosphate, butyl phosphate, (3) ethylene carbonate.

A mixture of such solvents can also be used.

The amount of organic solvent to be used is determined in such manner that the molar ratio between the number of moles of organic solvent and the number of moles of phenolic compound of formula (I) ranges from 0.01 to 0.25, and preferably from 0.025 to 0.15.

The amount of solvent to be added is selected as a function of the basicity of the solvent. The higher the basicity of the solvent, the smaller will be the amount used.

Stated differently, an amount in the vicinity of the lower limit of the range indicated above will be selected when the solvent has a high basicity.

According to the present invention, the hydroxylation reaction of the phenolic compound of formula (I) is carried out using hydrogen peroxide in the presence of a sulfonic acid polymer, a ketone compound of formula (II) and, optionally, in the presence of a polar, aprotic, organic solvent as described above.

From a practical point of view, the process according to the invention is simple to carry out, whether continuously or discontinuously.

In a preferred embodiment, the following order for the introduction of the reagents is observed: the phenolic compound of formula (I), optionally the complexing agent, the sulfonic polymer and then the ketone compound of formula (II).

The reaction medium is heated to the desired temperature and then the hydrogen peroxide solution is added progressively.

At the end of the reaction, the solid acid catalyst is separated via conventional solid/liquid separation techniques, preferably by filtration.

In respect of the unconverted phenolic compound and the ketone compound of formula (II), these are separated from the hydroxylation products by the usual means, in particular by distillation, and are recycled to the reaction zone.

Exemplary phenolic compounds of formula (I) include phenol, anisole, o-cresol, m-cresol, 2-methyoxy phenol.

The process of the present invention is particularly suitable for the preparation of hydroquinone and pyrocatechol from phenol.

The process of the present invention presents numerous advantages.

It is simpler to conduct, since the catalyst is separated out at the end of the reaction by simple filtration, and washing and extraction operations are avoided.

It therefore permits, during separation of the catalyst, avoiding use of an organic solvent, which is expensive and nonetheless has to be recovered.

Further, the process of the invention also provides energy savings, since it eliminates the distillation of the extraction solvent.

Finally, it should be noted that the heterogeneous catalytic system of the invention permits not only easy separation, but also recycling of the catalytic system.

With respect to the results obtained, the process of the invention permits diphenols to be produced with a good reaction yield, and under the preferred conditions described above, it produces a predominant amount of hydroquinone.

In order to further illustrate the present invention and the advantages thereof, the following specific examples are given, it being understood that same are intended only as illustrative and in nowise limitative.

In said examples, the following abbreviations have the following definitions:

$$TT = \frac{\text{number of moles of hydrogen peroxide converted}}{\text{number of moles of hydrogen peroxide introduced}} \%$$

$$RT_{HQ} = \frac{\text{number of moles of hydroquinone formed}}{\text{number of moles of hydrogen peroxide converted}} \%$$

$$RT_{PC} = \frac{\text{number of moles of pyrocatechol formed}}{\text{number of moles of hydrogen peroxide converted}} \%$$

EXAMPLES

The operating procedure described below was utilized in each of the following examples.

The following reagents were introduced into a 5 ml glass flask provided with central stirring, a condenser, a pouring funnel and a thermometer:

(i) 47 g (0.50 mole) of phenol, (ii) x g of a ketone compound having the formula (II), (iii) y g of a sulfonic polymer.

In certain examples, z g of a polar aprotic solvent was optionally also introduced.

The different amounts (x, y and z) are reported in the summary Tables below.

The reaction mixture was heated to the selected reaction temperature, 75° C., while maintaining it under stirring at 1,200 revs/min.

The aqueous solution of hydrogen peroxide, 70.5% by weight, was introduced over 2 minutes via the pouring funnel in an amount which is also reported in the Tables to follow.

The reaction mixture was maintained under agitation at 75° C. for the duration indicated in the Tables.

The reaction mixture was then cooled and determination of the reaction products was carried out: the residual hydrogen peroxide was determined by iodometry and the diphenols formed were determined by high performance liquid chromatography.

EXAMPLES 1 to 4

Comparative Examples (a) and (b)

In this series of examples, a resin marketed under the trademark TEMEX 50 W was employed as the catalyst and benzophenone was employed as the cocatalyst.

The TEMEX 50 W resin was a sulfonic resin in gel form having a particle size of 0.3 to 0.8 mm and having a concentration of acid sites of 5.55 milliequivalents of $H^+$ per gram of resin.

The examples were conducted according to the operating procedure given above.

All of the operating conditions and the results obtained are reported in the following Table (I)

TABLE I

Hydroxylation of phenol via $H_2O_2$/TEMEX 50 W resin/ketone compound of formula (II):

| Example | Ketone compound (II) [molar ratio ketone compound (II)/$H_2O_2$] | Organic solvent [molar ratio organic solvent/phenol] | Molar ratio $H_2O_2$/phenol | Molar ratio $H^+/H_2O_2$ | Duration | TT | $RT_{HQ}$ | $RT_{PC}$ | Ratio HQ/PC |
|---|---|---|---|---|---|---|---|---|---|
| 1 | benzophenone (0.99) | N/A | $5.05 \cdot 10^{-2}$ | $1.6 \cdot 10^{-2}$ | 3 hr, 35 min | 93 | 34.5 | 35.0 | 0.99 |
| 2 | benzophenone (3.80) | N/A | $5.2 \cdot 10^{-2}$ | $1.25 \cdot 10^{-2}$ | 4 hr | 95.5 | 39.0 | 37.0 | 1.05 |
| 3 | benzophenone (0.975) | acetonitrile (0.25) | $5.15 \cdot 10^{-2}$ | $2.7 \cdot 10^{-2}$ | 4 hr, 30 min | 91.0 | 36.5 | 33.0 | 1.11 |
| 4 | benzophenone (0.98) | nitrobenzene (0.25) | $5.15 \cdot 10^{-2}$ | $2.7 \cdot 10^{-2}$ | 3 hr, 30 min | 94.0 | 36.5 | 33.5 | 1.09 |
| (a) | N/A | N/A | $5.25 \cdot 10^{-2}$ | $1.6 \cdot 10^{-2}$ | 6 hr | 99.5 | 14.0 | 32.5 | 0.43 |
| (b) | acetophenone (1.0) | N/A | $5.0 \cdot 10^{-2}$ | $1.6 \cdot 10^{-2}$ | 2 hr | 100 | 37.0 | 48.0 | 0.77 |

For purposes of comparison, the results obtained are reported when the process of the invention was conducted:

Example (a): in the absence of benzophenone and the organic solvent,

Example (b): in the presence of acetophenone but in the absence of the organic solvent.

From Table I it will clearly be seen that the presence of the benzophenone permitted a good reaction yield and a greater amount of hydroquinone than pyrocatechol to be produced, in contradistinction to the processes of the prior art.

EXAMPLES 5 TO 10

Comparative Examples (c) and (d)

In the following examples, a resin marketed under the trademark AMBERLYST 15 was employed as the catalyst and benzophenone was employed as the cocatalyst.

The AMBERLYST 15 resin was a macroporous sulfonic resin having a particle size of 0.35 to 1.2 mm, an average pore diameter of 24 nm and having a concentration of acid sites of 4.44 milliequivalents of $H^+$ per gram of resin.

The examples were conducted according to the operating procedure given above.

All of the operating conditions and the results obtained are reported in the following Table (II):

TABLE II

Hydroxylation of phenol via $H_2O_2$/AMBERLYST 15 resin/ketone compound of formula (II):

| Example | Ketone compound (II) [molar ratio ketone compound (II)/$H_2O_2$] | Organic solvent [molar ratio organic solvent/phenol] | Molar ratio $H_2O_2$/phenol | Molar ratio $H^+/H_2O_2$ | Duration | TT | $RT_{HQ}$ | $RT_{PC}$ | Ratio HQ/PC |
|---|---|---|---|---|---|---|---|---|---|
| 5 | benzophenone (0.99) | N/A | $5.1 \cdot 10^{-2}$ | $1.65 \cdot 10^{-2}$ | 3 hr | 100 | 30.5 | 35.0 | 0.87 |
| 6 | benzophenone (0.975) | sulfolane (0.25) | $5.25 \cdot 10^{-2}$ | $2.8 \cdot 10^{-2}$ | 4 hr | 75.5 | 39.0 | 38.5 | 1.01 |
| 7 | benzophenone (0.985) | nitrobenzene (0.49) | $5.0 \cdot 10^{-2}$ | $5.7 \cdot 10^{-2}$ | 2 hr | 98.0 | 26.0 | 30.0 | 0.87 |
| 8 | benzophenone (0.99) | acetonitrile (0.46) | $4.7 \cdot 10^{-2}$ | $2.8 \cdot 10^{-2}$ | 4 hr | 99.0 | 29.0 | 30.5 | 0.95 |
| 9 | benzophenone (1.0) | propylene carbonate (0.25) | $5.0 \cdot 10^{-2}$ | $3.0 \cdot 10^{-2}$ | 1 hr, 30 min | 86.0 | 33.5 | 35.0 | 0.96 |
| 10 | benzophenone (0.98) | propylene carbonate (0.50) | $5.0 \cdot 10^{-2}$ | $5.6 \cdot 10^{-2}$ | 2 hr | 96.0 | 28.0 | 29.0 | 0.97 |

TABLE II-continued

Hydroxylation of phenol via $H_2O_2$/AMBERLYST 15 resin/ketone compound of formula (II):

| Example | Ketone compound (II) [molar ratio ketone compound (II)/$H_2O_2$] | Organic solvent [molar ratio organic solvent/phenol] | Molar ratio $H_2O_2$/phenol | Molar ratio $H^+$/$H_2O_2$ | Duration | TT | $RT_{HQ}$ | $RT_{PC}$ | Ratio HQ/PC |
|---|---|---|---|---|---|---|---|---|---|
| (c) | N/A | N/A | $5.3 \cdot 10^{-2}$ | $1.6 \cdot 10^{-2}$ | 4 hr, 15 min | 100 | 13.0 | 32.0 | 0.41 |
| (d) | acetophenone (0.94) | N/A | $5.3 \cdot 10^{-2}$ | $1.6 \cdot 10^{-2}$ | 1 hr, 15 min | 100 | 33.0 | 45.5 | 0.72 |

EXAMPLE 11

Comparative Examples (e) and (f)

The use of a resin marketed under the trademark AMBERLYST 35 as the catalyst and benzophenone as the cocatalyst is illustrated in the following examples.

The AMBERLYST 35 resin was a macroporous polysulfonic resin having a particle size of 0.4 to 1.25 mm, an average pore diameter of 20 nm and having a concentration of acid sites of 5.01 milliequivalents of $H^+$ per gram of resin.

The examples were conducted according to the operating procedure given above.

All of the operating conditions and the results obtained are reported in the following Table (III):

TABLE III

Hydroxylation of phenol via $H_2O_2$/AMBERLYST 35 resin/ketone compound of formula (II):

| Example | Ketone compound (II) [molar ratio ketone compound (II)/$H_2O_2$] | Organic solvent [molar ratio organic solvent/phenol] | Molar ratio $H_2O_2$/phenol | Molar ratio $H^+$/$H_2O_2$ | Duration | TT | $RT_{HQ}$ | $RT_{PC}$ | Ratio HQ/PC |
|---|---|---|---|---|---|---|---|---|---|
| 11 | benzophenone (0.955) | N/A | $4.9 \cdot 10^{-2}$ | $1.5 \cdot 10^{-2}$ | 3 hr | 100 | 31.5 | 35.5 | 0.89 |
| (e) | N/A | N/A | $5.2 \cdot 10^{-2}$ | $1.6 \cdot 10^{-2}$ | 5 hr | 100 | 15.0 | 33.5 | 0.45 |
| (f) | acetophenone (1.0) | N/A | $5.2 \cdot 10^{-2}$ | $1.5 \cdot 10^{-2}$ | 1 hr, 15 min | 100 | 35.0 | 46.5 | 0.75 |

EXAMPLE 12

Comparative Examples (g) and (h)

In the following examples a resin marketed under the trademark AMBERLYST 36 was used as the catalyst and benzophenone was used as the cocatalyst.

The AMBERLYST 36 resin was a macroporous polysulfonic resin having a particle size of 0.4 to 1.2 mm, an average pore diameter of 13 nm and having a concentration of acid sites of 5.12 milliequivalents of $H^+$ per gram of resin.

The examples were conducted according to the operating procedure given above.

All of the operating conditions and the results obtained are reported in the following Table (IV):

TABLE IV

Hydroxylation of phenol via $H_2O_2$/AMBERLYST 36 resin/ketone compound of formula (II):

| Example | Ketone compound (II) [molar ratio ketone compound (II)/$H_2O_2$] | Organic solvent [molar ratio organic solvent/phenol] | Molar ratio $H_2O_2$/phenol | Molar ratio $H^+$/$H_2O_2$ | Duration | TT | $RT_{HQ}$ | $RT_{PC}$ | Ratio HQ/PC |
|---|---|---|---|---|---|---|---|---|---|
| 12 | benzophenone (0.94) | N/A | $5.2 \cdot 10^{-2}$ | $1.5 \cdot 10^{-2}$ | 3 hr | 100 | 30.5 | 35.0 | 0.87 |
| (g) | acetophenone (0.975) | N/A | $5.1 \cdot 10^{-2}$ | $1.6 \cdot 10^{-2}$ | 1 hr, 30 min | 100 | 28.5 | 38.0 | 0.75 |
| (h) | N/A | N/A | $5.0 \cdot 10^{-2}$ | $1.6 \cdot 10^{-2}$ | 5 hr, 15 min | 99.0 | 15.0 | 35.0 | 0.43 |

EXAMPLE 13

Comparative Examples (i) and (j)

The use of a resin marketed under the trademark DUOLITE ARC 9359 as the catalyst and benzophenone as the cocatalyst is illustrated in the following examples.

The DUOLITE ARC 9359 resin was a phenol/formaldehyde resin substituted by a methylenesulfonic acid group on the aromatic nucleus. It had a concentration of acid sites of 2.73 milliequivalents of $H^+$ per gram of resin.

The examples were conducted according to the operating procedure given above.

All of the operating conditions and the results obtained are reported in the following Table (V):

TABLE V

Hydroxylation of phenol via $H_2O_2$/DUOLITE ARC 9359 resin/ketone compound of formula (II):

| Example | Ketone compound (II) [molar ratio ketone compound (II)/$H_2O_2$] | Organic solvent [molar ratio organic solvent/phenol] | Molar ratio $H_2O_2$/phenol | Molar ratio $H^+$/$H_2O_2$ | Duration | TT | $RT_{HQ}$ | $RT_{PC}$ | Ratio HQ/PC |
|---|---|---|---|---|---|---|---|---|---|
| 13 | benzophenone (0.97) | N/A | $5.0 \cdot 10^{-2}$ | $1.55 \cdot 10^{-2}$ | 2 h | 100 | 29.0 | 35.5 | 0.82 |
| (i) | acetophenone (1.0) | N/A | $5.4 \cdot 10^{-2}$ | $1.7 \cdot 10^{-2}$ | 0 hr, 30 min | 99.0 | 35.5 | 48.0 | 0.74 |
| (j) | N/A | N/A | $5.4 \cdot 10^{-2}$ | $1.5 \cdot 10^{-2}$ | 1 hr, | 100 | 7.5 | 29.0 | 0.26 |

TABLE V-continued

| | Hydroxylation of phenol via H$_2$O$_2$/DUOLITE ARC 9359 resin/ketone compound of formula (II): | | | | | | | | |
|---|---|---|---|---|---|---|---|---|---|
| Example | Ketone compound (II) [molar ratio ketone compound (II)/H$_2$O$_2$] | Organic solvent [molar ratio organic solvent/phenol] | Molar ratio H$_2$O$_2$/phenol | Molar ratio H$^+$/H$_2$O$_2$ | Duration | TT | RT$_{HQ}$ | RT$_{PC}$ | Ratio HQ/PC |
| | | | | | 30 min | | | | |

EXAMPLE 14

Comparative Examples (k) and (l)

In this series of examples, a resin marketed under the trademark DOWEX 50 W was used as the catalyst and benzophenone was used as the cocatalyst.

The DOWEX 50 W resin was a sulfonic resin in gel form having a particle size of 0.04 to 0.07 mm and having a concentration of acid sites of 4.51 milliequivalents of H$^+$ per gram of resin.

The examples were conducted according to the operating procedure given above.

All of the operating conditions and the results obtained are reported in the following Table (VI):

TABLE VI

| | Hydroxylation of phenol via H$_2$O$_2$/DOWEX 50 W resin/ketone compound of formula (II): | | | | | | | | |
|---|---|---|---|---|---|---|---|---|---|
| Example | Ketone compound (II) [molar ratio ketone compound (II)/H$_2$O$_2$] | Organic solvent [molar ratio organic solvent/phenol] | Molar ratio H$_2$O$_2$/phenol | Molar ratio H$^+$/H$_2$O$_2$ | Duration | TT | RT$_{HQ}$ | RT$_{PC}$ | Ratio HQ/PC |
| 14 | benzophenone (0.945) | N/A | $5.1 \cdot 10^{-2}$ | $1.5 \cdot 10^{-2}$ | 3 hr | 100 | 25.0 | 30.0 | 0.83 |
| (k) | acetophenone (0.935) | N/A | $5.6 \cdot 10^{-2}$ | $1.5 \cdot 10^{-2}$ | 1 hr | 99.5 | 30.0 | 42.5 | 0.71 |
| (l) | N/A | N/A | $5.2 \cdot 10^{-2}$ | $1.6 \cdot 10^{-2}$ | 3 hr | 99.5 | 6.5 | 22.0 | 0.29 |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the hydroxylation of an aromatic compound substituted with a —OR group and having a hydrogen atom in the para position to the —OR group, where R is a hydrogen atom or a hydrocarbon radical having from 1 to 24 carbon atoms, comprising reacting said aromatic compound with hydrogen peroxide, in the presence of a catalytically effective amount of a sulfonated polymer and a cocatalytically effective amount of a benzophenone compound having the Formula (II):

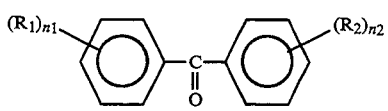

in which R$_1$ and R$_2$, which may be identical or different, are each a hydrogen atom or an electron-donor group, and n$_1$ and n$_2$, which may be identical or different, are each a number equal to 0, 1, 2 or 3, with the proviso that the two carbon atoms situated in the alpha position relative to the two carbon atoms from which the

group depends can be bonded together via a valence bond or via a —CH$_2$— bridge, thus forming a saturated or unsaturated ketone ring member.

2. The process as defined by claim 1, said sulfonated polymer comprising a sulfonated styrene/divinylbenzene copolymer, a sulfonated phenol/formaldehyde copolymer, or a tetrafluoroethylene-perfluoro[2-(fluorosulfonylethoxy)-propyl] vinyl ether copolymer.

3. The process as defined by claim 2, said sulfonated polymer comprising TEMEX 50, AMBERLYST 15, AMBERLYST 35, AMBERLYST 36, DOWEX 50 W, DUOLITE ARC 9359 or NAFION.

4. The process as defined by claim 1, said sulfonated polymer having a concentration of acid sites ranging from 1 to 10 milliequivalents of H$^+$ ions per gram of dry polymer.

5. The process as defined by claim 1, wherein said aromatic ketone having the formula (II), R$_1$ and R$_2$, which may be identical or different, are each a linear or branched alkyl radical having from 1 to 4 carbon atoms, a phenyl radical, an R$_3$—0— alkoxy radical in which R$_3$ is a linear or branched alkyl radical having from 1 to 4 carbon atoms or a phenyl radical, a hydroxyl group, or a fluorine atom.

6. The process as defined by claim 1, wherein said aromatic ketone having the formula (II), R$_1$ and R2, which may be identical or different, are each a hydrogen atom or an electron-donor group in the positions 4,4' and n$_1$ and n$_2$, which may be identical or different, are each 0 or 1.

7. The process as defined by claim 1, wherein said aromatic ketone having the formula (II), R$_1$ and R2, which may be identical or different, are each a hydrogen atom, a methyl, ethyl, tertiobutyl or phenyl radical, a methoxy or ethoxy radical, or a hydroxyl group.

8. The process as defined by claim 1, said aromatic ketone having the formula (II) comprising benzophenone, 2-methylbenzophenone, 2,4-dimethylbenzophenone, 4,4'-dimethylbenzophenone, 2,2'-dimethylbenzophenone, 4,4'-dimethoxybenzophenone, fluorenone, 4-hydroxybenzophenone, 4,4'-dihydroxybenzophenone or 4-benzoylbiphenyl.

9. The process as defined by claim 1, carried out in the presence of such amount of sulfonated polymer that the ratio of the number of proton equivalents thereof to the number of moles of hydrogen peroxide ranges from about $1.10^{-4}$ to about 1.0.

10. The process as defined by claim 9, carried out in the presence of such amount of aromatic ketone that the number of moles thereof per mole of hydrogen peroxide ranges from $1.10^{-3}$ to 10.

11. The process as defined by claim 1, carried out in the presence of a polar, aprotic, organic solvent having a dielectric constant of at least 20 and a donor number of less than 25.

12. The process as defined by claim 11, said polar organic solvent having a dielectric constant ranging from 25 to 75.

13. The process as defined by claim 11, said polar organic solvent having a donor number no greater than 20.

14. The process as defined by claim 11, said polar organic solvent comprising a nitro compound, an aliphatic or aromatic nitrile, tetramethylene sulfone, or propylene carbonate.

15. The process as defined by claim 14, said polar organic solvent comprising nitromethane, nitroethane, 1-nitropropane, 2-nitropropane, or mixture thereof, nitrobenzene, acetonitrile, propionitrile, butanenitrile, isobutanenitrile, benzonitrile, benzyl cyanide, tetramethylene sulfone, or propylene carbonate.

16. The process as defined by claim 11, carried out in the presence of such amount of polar organic solvent that the number of moles thereof to the number of moles of said phenolic compound ranges from 0.1 to 2.0.

17. The process as defined by claim 1, carried out in the presence of a polar, aprotic, organic solvent having a dielectric constant less than about 20 and a donor number of at least 15 but less than 25.

18. The process as defined by claim 17, said polar organic solvent having a dielectric constant ranging from 2 to 15.

19. The process as defined by claim 17, said polar organic solvent having a donor number ranging from 15 to 25.

20. The process as defined by claim 17, said polar organic solvent comprising an aliphatic, cycloaliphatic or aromatic ether-oxide, a neutral phosphoric ester, or ethylene carbonate.

21. The process as defined by claim 20, said polar organic solvent comprising diethyl oxide, dipropyl oxide, diisopropyl oxide, dibutyl oxide, methyltertiobutylether, dipentyl oxide, diisopentyl oxide, 1,2-dimethoxyethane, 1,5-dimethoxy-3-oxapentane, dioxane, tetrahydrofuran, trimethyl phosphate, triethyl phosphate, butyl phosphate, triisobutyl phosphate, tripentyl phosphate, or ethylene carbonate.

22. The process as defined by claim 11, carried out in the presence of such amount of polar organic solvent that the number of moles thereof to the number of moles of said phenolic compound ranges from 0.01 to 0.25.

23. The process as defined by claim 1, carried out at a temperature ranging from 45° to 150° C.

24. The process as defined by claim 1, said aromatic compound having the general formula (I):

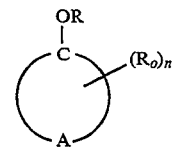

in which A is the residue of a monocyclic or polycyclic aromatic carbocyclic radical, or a divalent radical comprising at least two monocyclic aromatic carbocyclic radicals; R is a hydrogen atom or a linear or branched, saturated or unsaturated aliphatic radical, or a saturated or unsaturated or aromatic, monocyclic or polycyclic cycloaliphatic radical; $R^O$ is at least one nuclear substituent; and n is a number of 4 or less.

25. The process as defined by claim 24, wherein said aromatic compound having the formula (I), R is a hydrogen atom, a linear or branched alkyl radical having from 1 to 6 carbon atoms, a cyclohexyl radical, a phenyl radical, or a benzyl radical; and $R_O$ is a hydrogen atom, a linear or branched alkyl radical having from 1 to 6 carbon atoms, a linear or branched alkenyl radical having from 2 to 6 carbon atoms, an alkoxy radical $R_4$—O—, in which $R_4$ is a linear or branched alkyl radical having from 1 to 6 carbon atoms, an acyl radical having from 2 to 6 carbon atoms, a hydroxyl group, a —COOR$_5$ radical, in which R$_5$ is a linear or branched alkyl radical having from 1 to 4 carbon atoms, a halogen atom, or a —CF$_3$ radical.

26. The process as defined by claim 1, said aromatic compound having the general formula (I'):

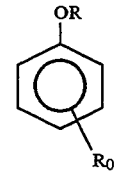

in which R and $R_o$, which may be identical or different, are each a hydrogen atom, an alkyl radical having from 1 to 4 carbon atoms, a cyclohexyl radical, or a phenyl radical.

27. The process as defined by claim 26, wherein said aromatic compound having the formula (I'), R is a hydrogen atom and $R_O$ is a hydrogen atom, or a methyl or methoxy radical.

28. The process as defined by claim 24, said aromatic compound comprising phenol, anisole, o-cresol, m-cresol, or 2-methoxyphenol.

29. The process as defined by claim 28, said aromatic compound comprising phenol.

30. The process as defined by claim 24, wherein said aromatic compound having the formula (I), the residue A is a monocyclic or polycyclic aromatic carbocyclic radical, the ring members of which can together form an orthocondensed radical having the formula (Ia):

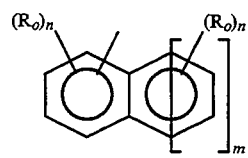

in which m is 0, 1 or 2; or a radical comprising at least two monocyclic aromatic carbocyclic radicals having the formula (Ib):

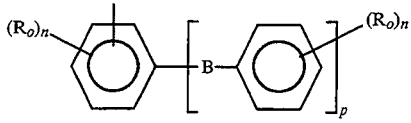

in which p is 0, 1, 2 or 3, and B is a valence bond, an alkylene or alkylidene radical having from 1 to 4 carbon atoms, or one of the groups of the formulae:

$$-O-, \quad -COO-, \quad -OCOO-, \quad -SO_2-, \quad -CO-\underset{R_6}{N}-$$

wherein $R_6$ is a hydrogen atom, an alkyl radical having from 1 to 4 carbon atoms, as a cyclohexyl or phenyl radical.

31. The process as defined by claim 30, wherein said formulae (Ia) and (Ib), $R_O$ is a hydrogen atom, a linear or branched alkyl or alkoxy radical having from 1 to 6 carbon atoms, a cyclohexyl radical, a phenyl radical, or a hydroxyl group; B is a valence bond, an alkylene or alkylidene radical having from 1 to 4 carbon atoms, or an oxygen atom; m is 0 or 1; is 0, 1 or 2; and p is 0 or 1.

* * * * *